United States Patent [19]

Toussaint et al.

[11] Patent Number: 5,015,788

[45] Date of Patent: May 14, 1991

[54] PROCESS FOR THE HYDROGENATION OF ACETYLENIC ALCOHOLS

[75] Inventors: Herbert Toussaint, Frankenthal; Juergen Schossig, Fussgoenheim; Heinz Graefje; Wolfgang Reiss, both of Ludwigshafen; Roland Spahl, Lorsch; Matthias Irgang, Heidelberg; Walter Himmel, Gruenstadt; Gerhard Koppenhoefer, Ludwigshafen, all of Fed. Rep. of Germany

[73] Assignee: BASF Aktiengesellschaft, Ludwigshafen, Fed. Rep. of Germany

[21] Appl. No.: 502,925

[22] Filed: Apr. 2, 1990

[30] Foreign Application Priority Data

Apr. 27, 1989 [DE] Fed. Rep. of Germany ....... 3913839

[51] Int. Cl.$^5$ .................... C07C 29/17; C07C 31/10; C07C 31/20
[52] U.S. Cl. .................... 568/861; 568/903
[58] Field of Search .................... 568/861, 903

[56] References Cited

U.S. PATENT DOCUMENTS

| | | |
|---|---|---|
| 3,449,445 | 6/1969 | Wetherill ..................... 260/635 |
| 3,691,093 | 9/1972 | Frank et al. ................. 568/861 |
| 4,072,714 | 2/1978 | Voges et al. ................. 568/861 |
| 4,213,000 | 7/1980 | Costes ........................ 568/861 |
| 4,287,099 | 9/1981 | Baer et al. .................. 252/465 |
| 4,384,147 | 5/1983 | Baer et al. .................. 568/861 |

FOREIGN PATENT DOCUMENTS

| | | |
|---|---|---|
| 18569 | 4/1982 | European Pat. Off. . |
| 2536273 | 2/1977 | Fed. Rep. of Germany . |

*Primary Examiner*—J. E. Evans
*Attorney, Agent, or Firm*—John H. Shurtleff

[57] ABSTRACT

A process for the preparation of saturated alcohols by catalytic hydrogenation of acetylenic alcohols at a temperature of from 50° to 200° C. and under a pressure of from 30 to 320 bar, wherein the catalyst used has a content of from 20 to 75% of nickel oxide, from 10 to 75% of zirconium dioxide and from 5 to 50% of copper oxide, by weight of the oxidic, unreduced catalyst.

9 Claims, No Drawings

PROCESS FOR THE HYDROGENATION OF ACETYLENIC ALCOHOLS

The present invention relates to a process for the preparation of saturated alcohols by catalytic hydrogenation of acetylenic alcohols.

Numerous catalysts have been proposed for the hydrogenation of unsaturated aliphatic compounds. For example, U.S. Pat. No. 3,449,445 discloses that but-2-yne-1,4-diol can be hydrogenated to 1,4-butanediol in good yields when use is made of a catalyst containing nickel, copper and manganese on silicon dioxide. However, when 1,4-butanediol is prepared by this process on an industrial scale, deposition of silicon dioxide occurs in the heat exchangers and pipelines, and the removal of such deposits unavoidably constitutes a highly laborious procedure.

Good results are obtained when acetylenic alcohols are hydrogenated using the unsupported catalyst described in DE-OS 2,536,276, which contains the oxides of nickel, copper, molybdenum and manganese. When but-2-yne-1,4-diol is hydrogenated to 1,4-butanediol, particularly favorable results are achieved by intensifying the reaction conditions (high hydrogen pressure and high temperature) at the expense, however, of an unwanted formation of butanol. In addition, catalysts shaped by extrusion or pelleting are not dimensionally stable under large-scale production conditions and quickly disintegrate.

According to EP 0,018,569, particularly desirable results are achieved in the hydrogenation of but-2-yne-1,4-diol using a hydrogenation catalyst containing oxides of the metals nickel, copper, molybdenum and manganese, when said catalyst has been prepared by precipitation of the metal salts, filtration, washing, drying and tempering, with the addition of a salt of aluminum or iron prior to the precipitation stage. However, when this catalyst is used industrially over long onstream periods, slow but steady disintegration thereof occurs.

There has thus been a need to provide a novel process for the hydrogenation of acetylenic alcohols, whereby such unsaturated alcohols, for example but-2-yne-1,4-diol, can be converted to the saturated forms, for example 1,4-butanediol, in high yields when operating in industrial plant over long on-stream periods, without incurring the aforementioned disadvantages.

The process of the present invention satisfies the above requirements to a high degree and produces saturated alcohols by catalytic hydrogenation of acetylenic alcohols at a temperature of from 50° to 200° C. and under a pressure of from 30 to 320 bar, the catalyst used being one which has a content of 20–75% of nickel oxide, 10–75% of zirconium dioxide and 5–50% of copper oxide, by weight of the oxidic, unreduced catalyst.

Suitable acetylenic alcohols for the preparation of said saturated, in particular dihydric, alcohols are all those available from conventional processes, for example but-2-yne-1,4-diol and propargyl alcohol.

The catalytic hydrogenation of the acetylenic alcohols is carried out with hydrogen in contact with the catalyst at a temperature of from 50° to 200° C., preferably from 80° to 180° C., and under a pressure of from 30 to 320 bar, preferably from 100 to 320 bar.

In its oxidic, unreduced form, the catalyst used in the present invention has, for example, the following composition: from 30 to 70%, preferably from 40 to 60% and more preferably from 35 to 55% w/w of nickel oxide, from 10 to 60%, preferably from 15 to 50% and more preferably from 25 to 45% w/w of zirconium dioxide, and from 5 to 40%, preferably from 10 to 35% and more preferably from 15 to 20% w/w of copper oxide. The catalyst may also contain, for example, from 0.1 to 5% w/w of molybdenum oxide and, for example, from 0 to 10% w/w of manganese oxide.

Our novel process is particularly well-suited for the hydrogenation of but-2-yne-1,4-diol to 1,4-butanediol, in which case it makes considerably longer on-stream periods possible and increases the throughput significantly.

The catalyst to be used in our novel process may be prepared, for example, by conventional precipitation of salts of the metals nickel, copper, zirconium and, if required, manganese from an aqueous solution at a temperature of from 30° to 90° C. and a pH of from 5 to 9, and filtration of the suspension, after which the filter cake is dried and then tempered at a temperature of from 300° to 700° C. The molybdenum is added in the form of ammonium heptamolybdate prior to the drying stage. Precipitation is effected by mixing an aqueous solution of salts, such as the nitrates, sulfates or acetates, of the metals nickel, copper, zirconium and, possibly, manganese with an aqueous solution of an alkali metal carbonate. The proportions of the metal salts are adjusted so as to give the aforementioned composition of the catalyst after tempering.

A portion of, say, up to 50% w/w of the water-soluble zirconium salt, based on the zirconium used, may be replaced by solid zirconium dioxide, which is either added to the aqueous metal salt solution prior to precipitation or is initially placed in the reaction vessel.

More specifically, the catalyst is prepared, for example, by stirring the aqueous solution of the metal salts together with an aqueous alkali metal carbonate solution, preferably a sodium carbonate solution, to cause precipitation of the metals in the form of a mixture of their hydroxides and carbonates. The concentration of metal salts in the metal salt solution is advantageously 30 to 40%.

The aqueous alkali metal carbonate solution has a concentration of, say, from 10 to 20% and preferably from 15 to 20% w/w. Precipitation is carried out at a temperature of from 30° to 90° C. and preferably from 70° to 90° C. and at a pH of from 7 to 9.

The resulting suspension is filtered, and the filter cake is washed with water until free from anions. It is then dried at, say, from 120° to 200° C., in a drying cabinet or spray drier. Preferably, the molybdenum is added to the moist filter cake in the form of ammonium heptamolybdate. The dried filter cake is tempered at a temperature of from 350° to 700° C., preferably from 400° to 600° C.

It is advantageous to shape the resulting catalyst composition before use by known pelleting or extrusion methods. For example, it can be pressed to pellets measuring 6×3 mm using a pelleting aid, preferably graphite. The pellets thus formed are tempered at a temperature of from 300° to 700° C., preferably from 400° to 600° C. The pellets have a loose weight of from 1,500 to 1,900 g/l, a porosity (as determined by water absorption) of from 0.2 to 0.4 ml/g and a hardness of 3,000 to 4,000 N/cm². Before it is used for the purpose of the invention, the catalyst thus obtained is subjected to reductive treatment with hydrogen at a temperature of from 200° to 350° C., preferably from 230° to 280° C., for example for a period of from 20 to 40 hours under a hydrogen pressure of from 1 to 300 bar and preferably from 100 to 15 bar.

The hydrogenation of said unsaturated compounds is carried out under the stated temperature and pressure conditions, for example in a reactor in which the catalyst is present in the form of a fixed bed. As is evident from the Examples below, considerably longer on-stream periods and higher throughputs are achieved than is the case when conventional catalysts are used.

We have found that the process of the invention also has the following surprising advantage:

after deactivation of the catalyst, which occurs only after very long on-stream periods, it can be virtually completely reactivated by treatment with water for from 8 to hours at a temperature of from 100° to 250° C., preferably from 100° to 200° C., and under a pressure of from 100 to 320 bar.

EXAMPLE

In the following Examples, the percentages are by weight.

EXAMPLE 1

(a) Preparation of the Catalyst

An aqueous solution of nickel nitrate, copper nitrate and zirconium acetate containing 4.48% of NiO, 1.52% of CuO and 2.82% of $ZrO_2$ was fed at a steady rate to a stirred vessel together with a 20% aqueous sodium carbonate solution at a temperature of 70° C. such that a pH of 7.0 was maintained (as measured with a glass electrode), to effect precipitation.

The resulting suspension was filtered, and the filter cake was washed with completely demineralized water until the electrical conductivity of the filtrate was approx. 20 $\mu$S. Ammonium heptamolybdate was then added to the moist filter cake in an amount adjusted to give the oxide mixture stated below. The filter cake was then dried at a temperature of 150° C. in a drying cabinet or spray drier. The hydroxide/carbonate mixture thus obtained was then tempered at a temperature of 500° C. for a period of 4 hours.

The resulting catalyst had the following composition: 50% NiO, 17% CuO, 1.5% $MoO_3$ and 31.5% $ZrO_2$. The powdered catalyst was mixed with graphite and pressed to pellets measuring 6×3 mm. These pellets had a porosity (as determined by water absorption) of 0.20 ml/g and a hardness of 3,500 $N/cm^2$.

(b) Hydrogenation of but-2-yne-1,4-diol

The catalyst obtained as described in a) above was reduced in a hydrogenation reactor at a temperature of 250° C. and under a hydrogen pressure of 150 bar. At a temperature of 150° C. and a hydrogen pressure of 250 bar, 5 parts by weight of a 50% aqueous solution of but-2-yne-1,4-diol were hydrogenated with 2,500 parts by volume (STP) of hydrogen in contact with 8 parts by volume of the catalyst, per hour. The feed of butynediol was diluted with 50 parts by volume per hour of recycled effluent in order to control the temperature in the reactor and establish the correct distribution of liquid across the catalyst bed. The heat of hydrogenation was removed via a heat exchanger installed in the liquid circuit. The excess gas obtained following separation of the gas phase from the liquid phase was replenished with fresh hydrogen and recycled to the reactor inlet.

The conversion of but-2-yne-1,4-diol was virtually 100%. By-products of the hydrogenation were, for example:

| | |
|---|---|
| butanol | <5% w/w |
| 2-methyl-1,4-butanediol | <0.2% w/w |
| but-2-ene-1,4-diol | <0.1% w/w |
| [2-(4-hydroxy)butoxy]oxalene | <0.3% w/w |
| 4-hydroxybutyraldehyde | <0.5% w/w |
| gamma-butyrolactone | <0.5% w/w |

(percentages based on anhydrous contents)

In order to effect further conversion of the last four partially hydrogenated compounds in the above list, the effluent mixture was passed once through a second hydrogenation stage containing the same catalyst, where it was post-hydrogenated at a temperature of 180° C. and under a hydrogen pressure of 250 bar.

The resulting product contained at least 94% w/w of 1,4-butanediol (based on anhydrous content) and was purified by distillation to give pure 1,4-butanediol. No distinct diminution of pressure was evident after an on-stream period of 3 months, when still no catalyst components were found in the mixture discharged from the reactor. Throughputs of butynediol were achieved which were three times higher than that obtained in the comparative test (c) described below.

(c) Comparative Test The hydrogenation described in b) above was repeated using the catalyst described in the Example of EP-PS 18,569. After only a few weeks on stream, it was necessary to remove the catalyst bed due to clogging.

EXAMPLE 2

The hydrogenation described in Example 1, section (b) was continued for a longer period of time. After an on-stream time of about 4 months it became evident that the catalyst of the invention was losing hydrogenating efficiency, this being chiefly due to deposits of inorganic components derived from the industrial butynediol solution used. The catalyst bed was flushed for 24 hours with condensate having a temperature of 200° C. This treatment restored the catalyst to virtually its original activity. The flushing water contained traces of zirconium dioxide and also, for example, 0.1% w/w of silicon, 0.03% w/w of sodium, 0.01% w/w of copper, and organic components (<5% w/w).

We claim:

1. A process for the preparation of saturated alcohols by catalytic hydrogenation of acetylenic alcohols at a temperature of from 50° to 200° C. and under a pressure of from 30 to 320 bar, wherein a catalyst is used which has a content of from 20 to 75% of nickel oxide, from 10 to 75% of zirconium oxide and from 5 to 50% of copper oxide, by weight of the oxidic, unreduced catalyst.

2. A process as claimed in claim 1, wherein 1,4-butanediol is prepared from but-2-yne-1,4-diol.

3. A process as claimed in claim 1, wherein when the catalyst has lost some of its activity it is reactivated by treatment with water at a temperature of from 100° to 200° C. and under a pressure of from 100 to 320 bar.

4. A process as claimed in claim 1, wherein the catalyst used has a content of from 30 to 70% of nickel oxide, from 10 to 60% of zirconium dioxide and from 5 to 40% of copper dioxide, by weight of the oxidic, unreduced catalyst.

5. A process as claimed in claim 1, wherein the catalyst used has a content of from 40 to 60% of nickel oxide, from 15 to 50% of zirconium dioxide and from 10 to 35% of copper oxide, by weight of the oxidic, unreduced catalyst.

6. A process as claimed in claim 1, wherein the catalyst used has a content of from 35 to 55% of nickel oxide, from 25 to 45% of zirconium dioxide and from 15 to 20% of copper oxide, by weight of the oxidic, unreduced catalyst.

7. A process as claimed in claim 1, which further contains from 0.1 to 5% of molybdenum oxide, by weight of the oxidic, unreduced catalyst.

8. A process as claimed in claim 1, which further contains up to 10% of manganese oxide, by weight of the oxidic, unreduced catalyst.

9. A process as claimed in claim 1, wherein the catalyst consists essentially of about 50% NiO, 17% CuO, 1.5% $MoO_3$ and 31.5% Zr, all percentages being approximate and based on the total weight of the oxidic, unreduced catalyst.

* * * * *